(12) United States Patent
Farin et al.

(10) Patent No.: US 10,136,918 B2
(45) Date of Patent: *Nov. 27, 2018

(54) LAPAROSCOPIC PORT

(71) Applicant: EON SURGICAL LTD, Tel-Aviv (IL)

(72) Inventors: Danny Farin, Hod-Ha'Sharon (IL); Yehuda Bachar, Givat-Shmuel (IL); Ronny Winshtein, Ramat-Hasharon (IL)

(73) Assignee: EON SURGICAL LTD., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/483,871

(22) Filed: Apr. 10, 2017

(65) Prior Publication Data
US 2017/0215920 A1    Aug. 3, 2017

Related U.S. Application Data

(63) Continuation of application No. 14/399,899, filed as application No. PCT/EP2013/059693 on May 9, 2013, now Pat. No. 9,645,852.

(60) Provisional application No. 61/644,456, filed on May 9, 2012.

(51) Int. Cl.
*A61B 1/32* (2006.01)
*A61B 17/34* (2006.01)
*A61B 17/00* (2006.01)

(52) U.S. Cl.
CPC ...... *A61B 17/3423* (2013.01); *A61B 17/3498* (2013.01); *A61B 2017/00862* (2013.01); *A61B 2017/3441* (2013.01); *A61B 2017/3464* (2013.01); *A61B 2017/3486* (2013.01)

(58) Field of Classification Search
CPC .......... A61B 17/0218; A61B 17/3421; A61B 17/3462; A61B 2017/3419; A61B 2017/3464; A61B 2017/3441
See application file for complete search history.

(56) References Cited

U.S. PATENT DOCUMENTS

| | | | |
|---|---|---|---|
| 4,655,752 A | 4/1987 | Honkanen et al. |
| 4,960,412 A | 10/1990 | Fink |
| 5,104,383 A | 4/1992 | Shichman |

(Continued)

FOREIGN PATENT DOCUMENTS

| | | |
|---|---|---|
| DE | 4303026 A1 | 8/1994 |
| DE | 202006005442 U1 | 7/2006 |

(Continued)

*Primary Examiner* — Eduardo C Robert
*Assistant Examiner* — Michelle C Eckman
(74) *Attorney, Agent, or Firm* — Baker Hostetler LLP

(57) ABSTRACT

A laparoscopic port is disclosed which includes a tubular member comprising a proximal end and a distal end and a lumen extending there between. At least one seal member provided in the lumen adapted to prevent pressurized gas flow from the distal end to the proximal end of the tubular member. The laparoscopic port further includes a shielding trigger positioned distal to the seal member in the lumen, the shielding trigger is shaped so as at least a proximal portion of the shielding trigger has a narrowing cross-section that extends towards the seal member, the proximal portion is adapted to actuate a reversibly opening and protection of the seal member upon a proximally projected pressure from a distal end of an artifact.

19 Claims, 5 Drawing Sheets

(56) References Cited

U.S. PATENT DOCUMENTS

| | | |
|---|---|---|
| 5,179,936 A | 1/1993 | O'Hara et al. |
| 5,197,955 A | 3/1993 | Stephens et al. |
| 5,211,370 A | 5/1993 | Powers |
| 5,226,891 A | 7/1993 | Bushatz et al. |
| 5,334,164 A | 8/1994 | Guy et al. |
| 5,360,417 A | 11/1994 | Gravener et al. |
| 5,364,372 A | 11/1994 | Danks et al. |
| 5,391,153 A | 2/1995 | Haber et al. |
| 5,431,635 A | 7/1995 | Yoon |
| 5,458,640 A | 10/1995 | Gerrone |
| 5,466,224 A | 11/1995 | Yoon |
| 5,476,475 A | 12/1995 | Gadberry |
| 5,496,280 A | 3/1996 | Vandenbroek et al. |
| 5,522,831 A | 6/1996 | Sleister et al. |
| 5,545,150 A | 8/1996 | Danks et al. |
| 5,584,850 A | 12/1996 | Hart et al. |
| 5,645,076 A | 7/1997 | Yoon |
| 5,645,556 A | 7/1997 | Yoon |
| 5,657,963 A | 8/1997 | Hinchliffe et al. |
| 5,662,615 A | 9/1997 | Blake, III |
| 5,720,730 A | 2/1998 | Blake, III |
| 5,720,759 A | 2/1998 | Green et al. |
| 5,779,697 A | 7/1998 | Glowa et al. |
| 5,788,676 A | 8/1998 | Yoon |
| 5,792,113 A | 8/1998 | Kramer et al. |
| 5,820,600 A | 10/1998 | Carlson et al. |
| 5,865,812 A | 2/1999 | Correia |
| 5,868,773 A | 2/1999 | Danks et al. |
| 5,957,888 A | 9/1999 | Hinchliffe |
| 5,980,544 A | 11/1999 | Vaitekunas |
| 5,989,224 A | 11/1999 | Exline et al. |
| 6,004,326 A | 12/1999 | Castro et al. |
| 6,228,061 B1 | 5/2001 | Flatland et al. |
| 6,258,065 B1 | 7/2001 | Dennis et al. |
| 7,828,775 B2 * | 11/2010 | Okoniewski ........ A61B 17/3421 604/167.01 |
| 8,221,363 B2 | 7/2012 | Jepson |
| 8,353,825 B2 | 1/2013 | Hammond et al. |
| 8,454,579 B2 | 6/2013 | Fangrow, Jr. |
| 9,333,332 B2 | 5/2016 | Eisenkolb et al. |
| 2002/0111585 A1 * | 8/2002 | Lafontaine ........ A61M 39/0606 604/167.06 |
| 2003/0139756 A1 | 7/2003 | Brustad |
| 2004/0064100 A1 | 4/2004 | Smith |
| 2004/0066008 A1 | 4/2004 | Smith |
| 2004/0068232 A1 | 4/2004 | Hart et al. |
| 2004/0106942 A1 | 6/2004 | Taylor et al. |
| 2004/0204682 A1 | 10/2004 | Smith |
| 2004/0230161 A1 | 11/2004 | Zeiner |
| 2004/0236347 A1 | 11/2004 | Karasawa |
| 2004/0260244 A1 | 12/2004 | Piechowicz et al. |
| 2005/0015043 A1 | 1/2005 | Stubbs et al. |
| 2005/0065475 A1 | 3/2005 | Hart et al. |
| 2005/0070946 A1 | 3/2005 | Franer et al. |
| 2005/0070947 A1 | 3/2005 | Franer et al. |
| 2005/0077688 A1 | 4/2005 | Voegele et al. |
| 2005/0077689 A1 | 4/2005 | Hueil |
| 2005/0131349 A1 | 6/2005 | Albrecht et al. |
| 2005/0171479 A1 | 8/2005 | Hruska et al. |
| 2005/0212221 A1 | 9/2005 | Smith et al. |
| 2005/0216028 A1 * | 9/2005 | Hart .................. A61B 17/3462 606/108 |
| 2005/0261661 A1 | 11/2005 | McFarlane |
| 2005/0277946 A1 | 12/2005 | Greenhalgh |
| 2006/0020281 A1 | 1/2006 | Smith |
| 2006/0041232 A1 | 2/2006 | Stearns et al. |
| 2006/0047284 A1 | 3/2006 | Gresham |
| 2006/0071432 A1 | 4/2006 | Staudner |
| 2006/0149305 A1 | 7/2006 | Cuevas et al. |
| 2006/0189920 A1 | 8/2006 | Seeh |
| 2006/0211992 A1 | 9/2006 | Prosek |
| 2006/0217665 A1 | 9/2006 | Prosek |
| 2006/0220325 A1 | 10/2006 | McFarlane |
| 2006/0224120 A1 | 10/2006 | Smith et al. |
| 2006/0229528 A1 | 10/2006 | Heske et al. |
| 2006/0241671 A1 * | 10/2006 | Greenhalgh ........ A61B 17/3423 606/191 |
| 2006/0276751 A1 | 12/2006 | Haberland et al. |
| 2007/0088275 A1 | 4/2007 | Stearns et al. |
| 2007/0088277 A1 * | 4/2007 | McGinley .......... A61B 17/3462 604/167.01 |
| 2007/0255218 A1 | 11/2007 | Franer |
| 2008/0033363 A1 | 2/2008 | Haberland et al. |
| 2008/0051739 A1 * | 2/2008 | McFarlane ........ A61B 17/3462 604/278 |
| 2008/0065021 A1 | 3/2008 | Jenkins et al. |
| 2008/0097332 A1 | 4/2008 | Greenhalgh et al. |
| 2008/0157017 A1 | 7/2008 | Macatangay et al. |
| 2008/0171988 A1 * | 7/2008 | Blanco ............... A61B 17/3462 604/167.03 |
| 2008/0228207 A1 | 9/2008 | Kadykowski et al. |
| 2008/0249475 A1 | 10/2008 | Albrecht et al. |
| 2008/0294112 A1 | 11/2008 | Judson et al. |
| 2008/0294184 A1 | 11/2008 | Smith |
| 2008/0294186 A1 | 11/2008 | Judson et al. |
| 2008/0300455 A1 | 12/2008 | Smith |
| 2008/0300545 A1 | 12/2008 | Hsieh |
| 2009/0005738 A1 | 1/2009 | Franer |
| 2009/0076464 A1 | 3/2009 | Gresham |
| 2009/0093682 A1 | 4/2009 | Izzo et al. |
| 2009/0093683 A1 | 4/2009 | Richard et al. |
| 2009/0105635 A1 | 4/2009 | Bettuchi et al. |
| 2009/0137943 A1 | 5/2009 | Stearns et al. |
| 2009/0149813 A1 | 6/2009 | Franer et al. |
| 2009/0192465 A1 | 7/2009 | Smith |
| 2009/0209912 A1 * | 8/2009 | Keyser ............. A61M 25/0606 604/164.1 |
| 2009/0234293 A1 | 9/2009 | Albrecht et al. |
| 2009/0240204 A1 | 9/2009 | Taylor et al. |
| 2009/0259184 A1 | 10/2009 | Okoniewski |
| 2009/0259185 A1 | 10/2009 | Okoniewski |
| 2009/0270681 A1 | 10/2009 | Moreno et al. |
| 2009/0270685 A1 | 10/2009 | Moreno et al. |
| 2009/0270686 A1 | 10/2009 | Duke et al. |
| 2009/0270813 A1 | 10/2009 | Moreno, Jr. et al. |
| 2009/0270817 A1 | 10/2009 | Moreno et al. |
| 2009/0270818 A1 | 10/2009 | Duke |
| 2009/0281478 A1 | 11/2009 | Duke |
| 2009/0306697 A1 | 12/2009 | Fischvogt |
| 2009/0326463 A1 | 12/2009 | Ross |
| 2010/0004600 A1 | 1/2010 | Rockrohr et al. |
| 2010/0010444 A1 | 1/2010 | Bettuchi |
| 2010/0016799 A1 | 1/2010 | Schweitzer et al. |
| 2010/0022958 A1 * | 1/2010 | Moreno, Jr. ........ A61B 1/00128 604/165.02 |
| 2010/0049145 A1 * | 2/2010 | Teichtmann ........ A61B 17/3462 604/256 |
| 2010/0179479 A1 * | 7/2010 | Albrecht ............ A61B 17/3462 604/167.01 |
| 2010/0185139 A1 | 7/2010 | Stearns et al. |
| 2010/0240957 A1 * | 9/2010 | Abrams ............. A61B 17/3462 600/201 |
| 2010/0240958 A1 | 9/2010 | Abrams et al. |
| 2010/0240960 A1 | 9/2010 | Richard |
| 2010/0241061 A1 | 9/2010 | Ott et al. |
| 2010/0241079 A1 * | 9/2010 | Abrams ............. A61B 17/3462 604/167.01 |
| 2010/0249515 A1 | 9/2010 | Hudon et al. |
| 2010/0249711 A1 | 9/2010 | Fischvogt |
| 2010/0261969 A1 | 10/2010 | Fischvogt et al. |
| 2010/0261970 A1 | 10/2010 | Shelton et al. |
| 2010/0298774 A1 | 11/2010 | Igov |
| 2011/0046449 A1 * | 2/2011 | Minnelli ............. A61B 1/00128 600/205 |
| 2011/0054261 A1 | 3/2011 | Battles |
| 2011/0054405 A1 | 3/2011 | Whiting et al. |
| 2011/0087159 A1 | 4/2011 | Parihar et al. |
| 2011/0087168 A1 | 4/2011 | Parihar et al. |
| 2011/0087169 A1 | 4/2011 | Parihar et al. |
| 2011/0087170 A1 | 4/2011 | Insignares |
| 2011/0092910 A1 | 4/2011 | Schultz |
| 2011/0152622 A1 | 6/2011 | Brockmeier et al. |
| 2011/0152625 A1 | 6/2011 | Smith |

(56) References Cited

U.S. PATENT DOCUMENTS

| | | |
|---|---|---|
| 2011/0152776 A1 | 6/2011 | Hartoumbekis et al. |
| 2011/0202008 A1* | 8/2011 | Okoniewski ....... A61B 17/3462 604/167.03 |
| 2011/0208007 A1* | 8/2011 | Shohat ............... A61B 17/3403 600/227 |
| 2011/0237901 A1 | 9/2011 | Duke et al. |
| 2012/0004613 A1 | 1/2012 | Franer |
| 2012/0010569 A1 | 1/2012 | Parihar |
| 2012/0089094 A1 | 4/2012 | Franer et al. |
| 2012/0238825 A1* | 9/2012 | Smith ................ A61B 17/3423 600/207 |
| 2012/0296358 A1 | 11/2012 | Nguyen et al. |
| 2012/0316510 A1 | 12/2012 | Ott et al. |
| 2012/0316512 A1 | 12/2012 | Ott et al. |
| 2012/0316575 A1* | 12/2012 | Farin ................ A61B 17/00234 606/130 |
| 2013/0190572 A1 | 7/2013 | Lee |
| 2013/0310766 A1 | 11/2013 | Kleyman et al. |
| 2013/0310773 A1 | 11/2013 | Richard et al. |
| 2013/0345637 A1 | 12/2013 | Pauli et al. |
| 2014/0005474 A1* | 1/2014 | Farin .................. A61B 1/00154 600/104 |
| 2014/0018631 A1* | 1/2014 | Kleyman ........... A61B 17/3462 600/208 |
| 2014/0024896 A1 | 1/2014 | West |
| 2014/0024899 A1 | 1/2014 | Kleyman |
| 2014/0039263 A1 | 2/2014 | Le |
| 2014/0066711 A1* | 3/2014 | Farin .................... A61B 1/0684 600/109 |
| 2014/0088491 A1 | 3/2014 | Azarbarzin et al. |
| 2014/0194833 A1* | 7/2014 | Andrus .............. A61B 17/0218 604/288.02 |
| 2014/0235949 A1 | 8/2014 | Smith |
| 2014/0243599 A1* | 8/2014 | Farin ..................... A61B 17/34 600/114 |
| 2014/0276437 A1 | 9/2014 | Hart et al. |
| 2014/0316200 A1 | 10/2014 | Maxwell et al. |
| 2014/0323809 A1 | 10/2014 | Bonadio et al. |
| 2014/0343365 A1 | 11/2014 | Bachar et al. |
| 2014/0357958 A1 | 12/2014 | Eltoft et al. |
| 2014/0371681 A1 | 12/2014 | Yi |
| 2015/0025477 A1 | 1/2015 | Evans |
| 2015/0031958 A1 | 1/2015 | Kleyman |
| 2015/0038793 A1 | 2/2015 | Prior et al. |
| 2015/0045623 A1 | 2/2015 | Fischvogt |
| 2015/0073221 A1 | 3/2015 | Nuzziello |
| 2015/0164547 A1 | 6/2015 | Sauter et al. |
| 2015/0216560 A1 | 8/2015 | Holsten et al. |
| 2015/0216644 A1 | 8/2015 | Cahill et al. |
| 2015/0223833 A1 | 8/2015 | Coffeen et al. |
| 2016/0008591 A1 | 1/2016 | Furnish et al. |
| 2016/0015893 A1 | 1/2016 | Hoyt et al. |
| 2016/0045220 A1 | 2/2016 | Wachli et al. |
| 2016/0051281 A1 | 2/2016 | Hart et al. |
| 2016/0081715 A1 | 3/2016 | Kleyman |
| 2016/0089181 A1 | 3/2016 | Johnson |
| 2016/0100857 A1 | 4/2016 | Wachli et al. |
| 2016/0100858 A1 | 4/2016 | Flom et al. |
| 2017/0215920 A1* | 8/2017 | Farin ................. A61B 17/3423 |

FOREIGN PATENT DOCUMENTS

| | | |
|---|---|---|
| EP | 2143393 A1 | 1/2010 |
| WO | 2010081105 A1 | 7/2010 |
| WO | 2012035524 A2 | 3/2012 |

\* cited by examiner

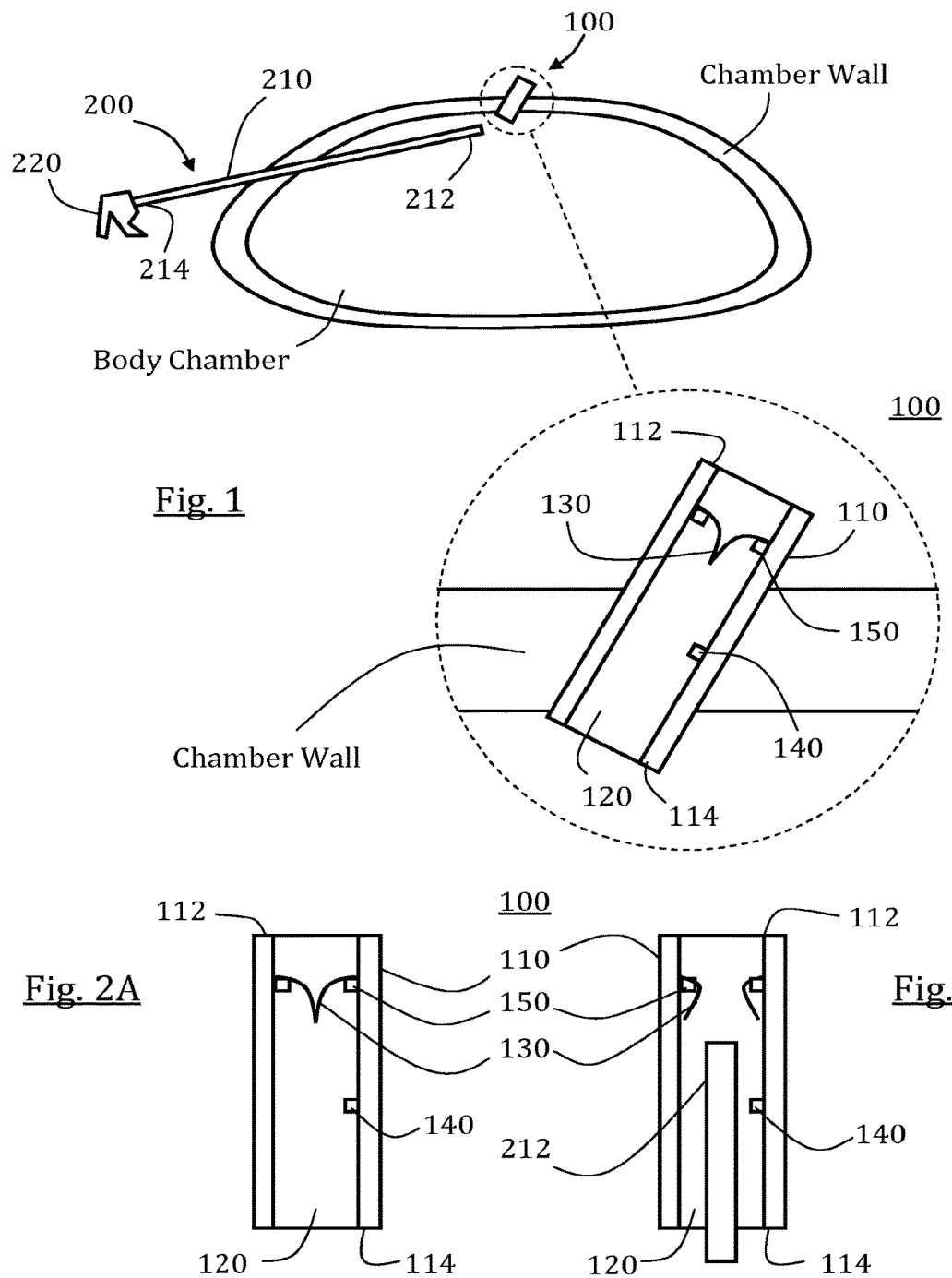

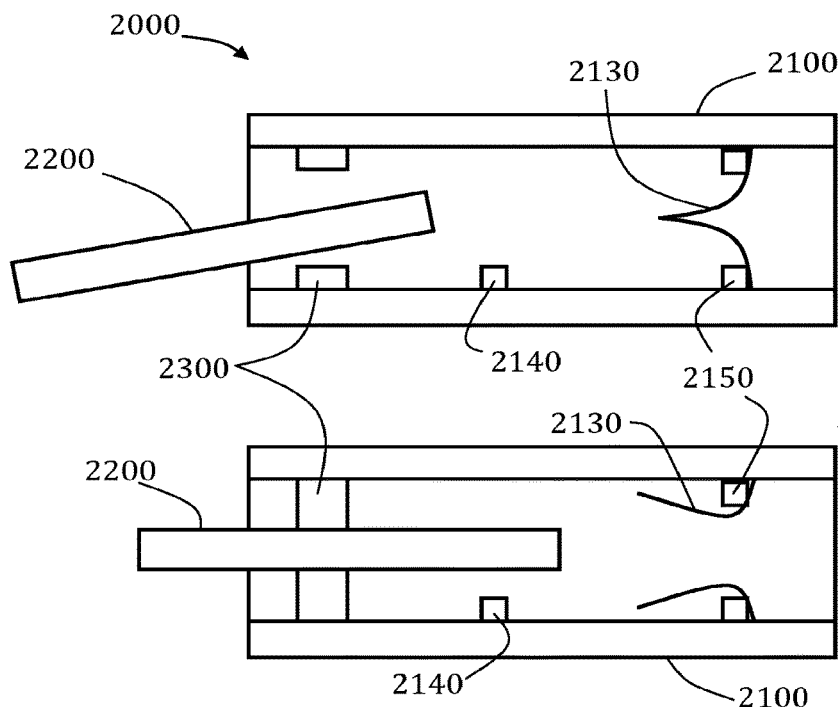
Fig. 3A
Fig. 3B
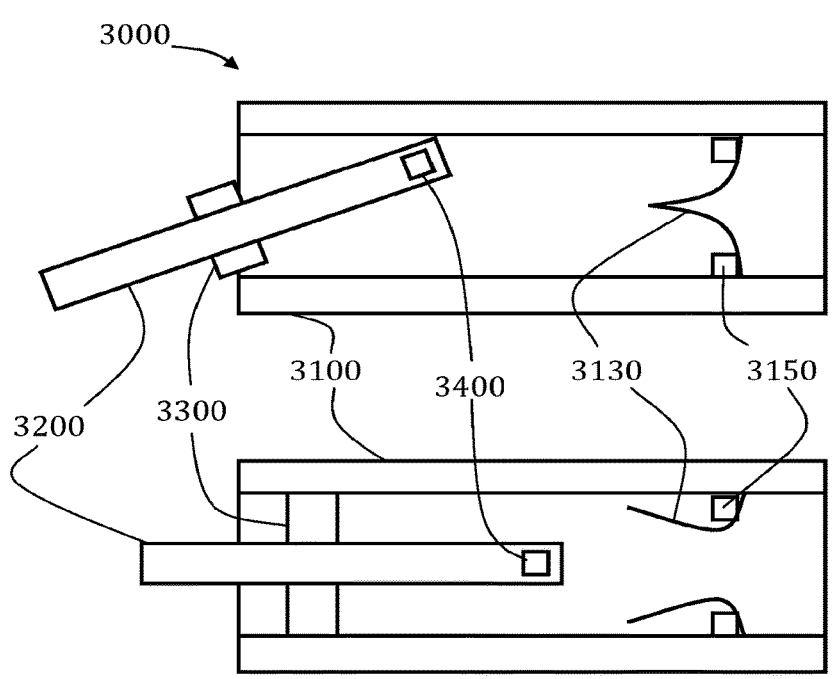
Fig. 4A
Fig. 4B

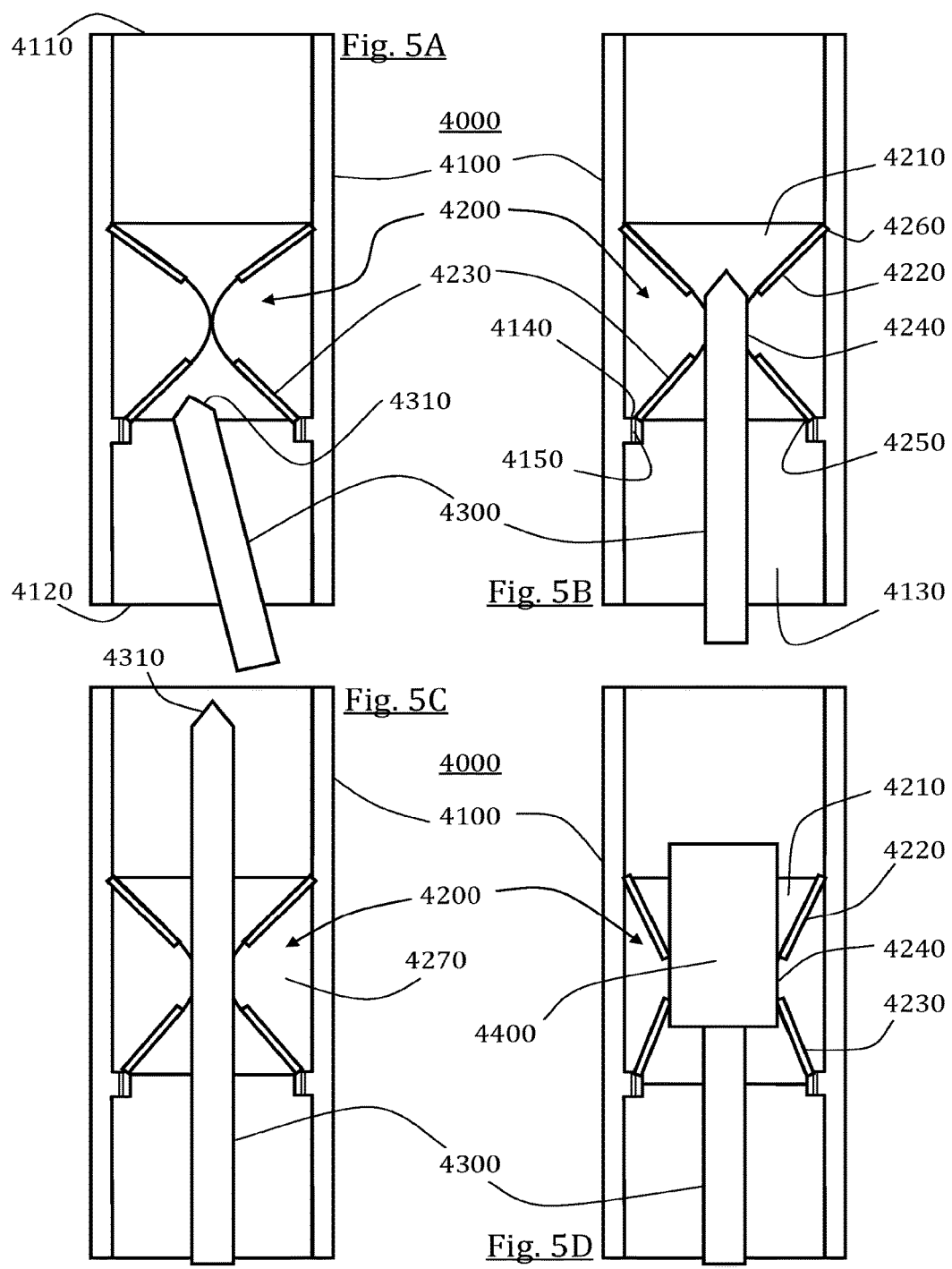

LAPAROSCOPIC PORT

CROSS-REFERENCE TO RELATED APPLICATIONS

This application is a continuation patent application of U.S. patent application Ser. No. 14/399,899, filed on Nov. 7, 2015, which is a National Stage of International Patent Application No. PCT/EP2013/059693, filed on May 9, 2013, which claims priority to U.S. Provisional Patent Application No. 61/644,456, filed on May 9, 2012, the disclosures of which are incorporated by reference in their entirety.

FIELD AND BACKGROUND

The present invention, in some embodiments thereof, relates to surgical devices, and in particular to systems and devices that include laparoscopic ports.

In common practice, laparoscopic surgery (or "laparoscopy") is performed using slender shafts with surgical tools that are introduced into the body via a laparoscopic port which provides a direct channel between a bodily chamber (e.g., abdominal cavity) and outer environment. In Micro-laparoscopy, thinner shafts are used, being of 3 mm or less diameter, and are provided with or connectable with surgical tool heads (optionally, detachable end-effectors). Regular sized surgical tools or tool heads may be of 3 mm to 20 mm in diameter, but more commonly between 5 mm and 12 mm.

International Patent Application No. PCT/IB2011/054102, the disclosure of which is fully incorporated herein by reference, describes method and means to assemble an end-effector to a distal end of a micro-sized shaft by initially introducing the shaft into the abdominal cavity in an entry point that is distant to a laparoscopic port; then pushing the shaft distal end outside the abdominal cavity through an the laparoscopic port; assembling the end-effector onto the shaft distal end under direct vision outside the abdominal cavity; and pulling the assembled device back into the abdominal cavity. In some embodiments thereof, guiding means are described for allowing direct passage for the shaft and/or end-effectors from a chosen point in the abdominal cavity to and through the laparoscopic port to outer environment. In some embodiments thereof, such guiding means are used also to bypass gas sealing or valve mechanism of the laparoscopic port.

SUMMARY

According to an aspect of some embodiments of the present invention there is provided a laparoscopic port. The laparoscopic port includes a tubular member comprising a proximal end and a distal end and a lumen extending there between. The laparoscopic port further includes at least one seal member provided in the lumen adapted to prevent pressurized gas flow from the distal end to the proximal end of the tubular member. The laparoscopic port also includes a shielding trigger positioned distal to the seal member in the lumen, the shielding trigger is shaped so as at least a proximal portion of the shielding trigger has a narrowing cross-section that extends towards the seal member, the proximal portion is adapted to actuate a reversibly opening and protection of the seal member upon a proximally projected pressure from a distal end of an artifact. The artifact may include a longitudinal shaft having a maximal outer diameter at a free end portion thereof, optionally 12 mm or less, optionally 5 mm or less.

According to another aspect of some embodiments of the present invention there is provided a method of opening and protecting a seal member in a laparoscopic port from being damaged by an artifact. The method includes providing a shielding trigger distally to the sealing member, wherein a proximal end of the shielding trigger is laterally extendable. The method further includes projecting a proximal pressure by a distal end of the artifact against a distal side of the shielding trigger, whereby the proximal end of the shielding trigger extends laterally opening and protecting the seal member.

Further embodiments of the invention are defined in the dependent claims, wherein features for the second and subsequent aspects of the invention are as for the first aspect mutatis mutandis.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 schematically illustrates a cut view of exemplary laparoscopic port and surgical manipulator deployed in a body chamber, in accordance with embodiments of the present invention;

FIGS. 2A-B schematically illustrate cut views of an exemplary laparoscopic port before and after sensing an incoming artifact traveling therethrough, in accordance with embodiments of the present invention;

FIGS. 3A-B schematically illustrate cut views of an exemplary laparoscopic port comprising triggering and centering means, before and after triggering, in accordance with some embodiments of the present invention;

FIGS. 4A-B schematically illustrate cut views of an exemplary laparoscopic port configured for triggering with an artifact comprising triggering and centering means, before and after triggering, in accordance with embodiments of the present invention;

FIGS. 5A-D schematically illustrate cut views of an exemplary laparoscopic port comprising a membrane type self-triggering valve mechanism, in accordance with embodiments of the present invention;

DESCRIPTION OF EMBODIMENTS

Figure 6A:
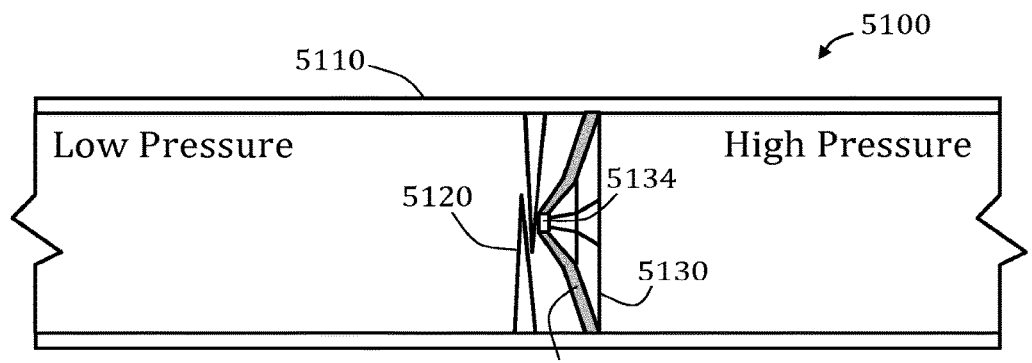
FIGS. 6A-B schematically illustrate cut views of portions of exemplary laparoscopic ports comprising distal seal protectors, in accordance with embodiments of the present invention.

The following preferred embodiments may be described in the context of exemplary laparoscopic or micro-laparoscopic surgical procedures for ease of description and understanding. However, the invention is not limited to the specifically described devices and methods, and may be adapted to various clinical applications without departing from the overall scope of the invention. For example, devices and related methods including concepts described herein may be used for other surgical procedures such as but not limited to: classic laparoscopic surgery, single-port laparoscopy, and NOTES assisted endoscopic or laparoscopic surgeries.

An aspect of some embodiments of the present invention relates to a laparoscopic port adapted to link a body chamber and outer environment. Reference is made to FIG. 1, which schematically illustrates a cut view of an exemplary laparoscopic port 100 and a surgical manipulator 200 deployed in a body chamber enclosed in a chamber wall, in accordance with embodiments of the present invention. Surgical manipulator 200 includes an elongated slender shaft 210 having a distal free end 212 and a proximal end 214 (shown for illustrative purposes connected to a manually operable handle 220). Shaft 210 and/or distal end 212 may include a maximal outer diameter of optionally 12 mm or less, optionally 5 mm or less, optionally 3 mm or less, optionally between 1 mm and 5 mm, optionally between 1.5 mm and 2.5 mm. Surgical manipulator 200 is shown and described for exemplary illustrative purposes and by no means limits the scope of the invention to manually operable laparoscopic surgeries. Shaft 210 may be manually or robotically operated as a laparoscopic surgical tool manipulator or a needle, with or without a surgical end-effector connected thereto.

Laparoscopic port 100 includes a tubular member 110 having a lumen 120 extending between a proximal end 112 and a distal end 114 thereof. A valve 130 is provided in lumen 120, optionally fixed to inner peripheral portions of tubular member 110 enclosing lumen 120. In some embodiments of the invention, valve 130 is adapted to normally prevent pressurized gas flow therethrough from distal end 114 to proximal end 112. Valve 130 may include a single resilient sealing device or material (e.g., a membrane) or include a plurality of different sealing members provided in sequence along a length in lumen 120. Valve 130 may include at least one instrument sealing member, as a one defining a central aperture radially stretchable around a shaft or an instrument periphery, and at least one zero closure sealing member (not shown). In some embodiments of the invention, valve 130 is configured to accommodate a length of an artifact travelling therethrough inwardly projecting in the lumen through the distal end, for example distal end 212 of surgical manipulator 200.

In some embodiments of the invention, a trigger 140 is provided distal to valve 130 and is adapted to trigger opening of the valve and/or any sealing member thereof in association with an incoming artifact inwardly projecting in lumen 120 through distal end 114. As described, an artifact may be any man-made or partially man-made instrument, for example a shaft, a needle, a surgical tool, a laparoscopic instrument or others. In some embodiments of the invention, a sensor is provided as or in combination with the trigger and is adapted to sense a parameter associated with the incoming artifact. Optionally, the sensor is at least one of: a mechanical sensor, a probe, an antenna, an electric sensor, a proximity sensor, a magnetic sensor, a pressure sensor, an optical sensor and an acoustic sensor. In some embodiments, the trigger and/or the sensor is provided in the lumen, or alternatively provided on the artifact. Reference is made to FIGS. 2A-B which schematically illustrate cut views of laparoscopic port 100 before and after sensing an incoming artifact traveling therethrough, in accordance with embodiments of the present invention. Optionally, the sensor is trigger 140 or is part of trigger 140 (as shown in FIGS. 1 and 2), or is apart from the trigger 140, or is provided instead of the trigger 140 (not shown).

In some embodiments of the invention, a valve actuator 150 is provided linked to trigger and/or sensor 140 and is adapted to open valve 130 at or following the triggering to thereby allow the pressurized flow therethrough (as shown in FIG. 2B). Optionally the link WSAfincludes a mechanical and/or electrical direct connection or alternatively a wireless connection. In some embodiments of the invention, valve 130 is triggered to accommodate an incoming artifact distal end before physical contact is made therebetween, therefore, optionally, leakage of pressurized gas from within the bodily chamber may occur or increase. In some embodiments, means are provided (not shown) to change (e.g., increase) flow regime or at least one parameter of gas flow into the bodily chamber. In some embodiments, a gas pressure controller is provided (not shown) linking between laparoscopic port 100 and a gas source, which are adapted for changing a flow parameter of gas flowing into the bodily chamber following the triggering.

In some embodiments of the invention, centering means are provided and are adapted to align the artifact in a chosen alignment, optionally in concentricity, with an axis of the lumen. Reference is now made to FIGS. 3A-B which schematically illustrate cut views of an exemplary laparoscopic port 2000 comprising triggering and centering means, before and after triggering, in accordance with some embodiments of the present invention. Laparoscopic port 2000 includes a hollow body 2100 that is opened at both ends and incorporating a valve 2130 that is selectively openable by actuator 2150 connected thereto. In some embodiments, valve 2130 is normally closed at positive pressure difference between its distal side and its proximal side, if over a predetermined threshold value. Alternatively and optionally, valve 2130 is selectively closed per-demand using actuator 2150. Laparoscopic port 2000 further includes a sensory trigger 2140 connected and positioned distally to actuator 2150, the trigger is adapted to command actuator 2150 to open valve 2130 when or as long as an object is positioned and/or passes in a predetermine sensing (e.g., proximity) range thereto and/or in line of sight. Centering mechanism 2300 is shown positioned distal to sensory trigger 2140 although it may be positioned proximal thereto. Alternatively, the centering mechanism may be positioned at the same location as the sensory trigger. In some embodiments of the invention, centering mechanism 2300 includes an expandable portion that may optionally expand at and/or following the sensing, and/or before the valve opening. Optionally, the expandable portion is inflatable. As shown in FIG. 3A, a longitudinal artifact 2200, characterized in a maximal diameter smaller than minimal inner diameter of laparoscopic port 2000, is angularly protruding into laparoscopic port 2000 lumen prior to reaching a sensing range of sensory trigger 2140. At that stage valve 2130 is maintained closed and prevents gas from flowing from a distal side to a proximal side thereof under normal conditions. If artifact 2200 was to travel still non-aligned through valve 2130 it may have caused damage and/or prevent appropriate sealing thereupon its periphery. As shown in FIG. 3B, artifact 2200 is further protruded in laparoscopic port 2000 after a sensing-triggering-actuating sequence occurred following sensing thereof by sensory trigger 2140 and ending with opening of valve 2130 to accommodate artifact 2200 to travel therethrough. Furthermore, sensory trigger 2140 has also initiated inward expansion of centering mechanism 2300 to thereby center artifact 2200 and align it with the longitudinal axis of laparoscopic port 2000.

Reference is now made to FIGS. 4A-B which schematically illustrate cut views of an exemplary laparoscopic port 3000 configured for triggering with an artifact 3200 comprising triggering and centering means, shown before (FIG. 4A) and after (FIG. 4B) triggering, in accordance with embodiments of the present invention. Laparoscopic port 3000 includes a hollow body 3100 that is opened at both ends and incorporating a valve 3130 that is selectively openable by actuator 3150 connected thereto. In some embodiments, valve 3130 is normally closed at positive pressure difference between its distal side and its proximal side, if over a predetermined threshold value. Alternatively and optionally, valve 3130 is selectively closed per-demand using actuator 3150. In some embodiments, actuator 3150 incorporates sensory and/or triggering means embedded thereto so that actuation of valve 3130 is initiated at artifact proximity or otherwise, actuator 3150 is wirelessly communicatable with sensory triggering means provided with the artifact as described hereinafter. Elongated artifact 3200 includes a sensory trigger 3400 provided adjacent its free end, the trigger is adapted to command actuator 3150 to open valve 3130 when or as long as it is positioned and/or passes in a predetermine sensing (e.g., proximity) range thereto and/or in line of sight. Optionally and alternatively, a code signaling or receivable device (e.g., an RFID tag; not shown) is provided instead of sensory trigger 3400 and is adapted to wirelessly communicating with a sensory type actuator. Artifact 3200 also includes a centering mechanism 3300 optionally including an expandable portion that may optionally expand at and/or following the sensing, and/or before the valve opening. Optionally, the expandable portion is inflatable. As shown in FIG. 4A, longitudinal artifact 3200 is angularly protruding into laparoscopic port 3000 lumen prior to reaching a sensing range between sensory trigger 3400 and actuator 3150. At that stage valve 3130 is maintained closed and prevents gas from flowing from a distal side to a proximal side thereof under normal conditions. As shown in FIG. 4B, artifact 3200 is further protruded in laparoscopic port 3000 after a sensing-triggering-actuating sequence occurred following sensing of actuator 3150 thereof by sensory trigger 3400 and ending with opening of valve 3130 to accommodate artifact 3200 to travel therethrough. Furthermore, sensory trigger 3400 has also initiated outward expansion of centering mechanism 3300 to thereby center artifact 3200 and align it with the longitudinal axis of laparoscopic port 3000.

In some embodiments of the invention, a valve incorporates at least one, optionally at least two, optionally all sensing, triggering, centering and actuating functions. A trigger of the present invention, for example a mechanical trigger, may also be applied for sensing a contacting and/or pressing artifact and/or actuate an initial, a partial or a full opening of a seal in the valve. The valve may include a plurality of seals, optionally distributed sequentially, optionally including at least one zero seal and/or at least one instrument seal. The trigger may be designed to statically and/or dynamically alter direction and/or align and center the artifact passing therealong or therethrough. The trigger may also be used or provided as a shield for a portion of a resilient member, such as the seal or a portion thereof, of the valve, especially if it is formed of a hardened material (e.g., a hard metal or plastic) and/or a reinforced pliant or semi-pliant material. As such, the trigger may be considered a "shielding trigger". Such a shielding trigger may be provided between an incoming artifact and the resilient member thereby preventing potential damage to the resilient member by the artifact, especially if the artifact includes a sharpened or otherwise hazardous contacting portion or free end. In some embodiments, at least one shielding trigger is provided about, in or adjacent a distal end of the valve, or to the resilient member or the seal, to thereby shield from a distal-to-proximal incoming artifact through laparoscopic port lumen.

Reference is now made to FIGS. 5A-D which schematically illustrate cut views of an exemplary laparoscopic port 4000 comprising a membrane type self-triggering valve 4200, in accordance with embodiments of the present invention. Laparoscopic port 4000 includes an elongated body 4100 having a lumen 4130 passing therethrough and opened at a proximal end 4110 and a distal end 4120. A circumferential projection 4140 inwardly and radially projects from body 4100 wall in lumen 4130 and comprising a plurality (but optionally only one) of through-openings 4150. Pressurizing means (not shown) may be applied with laparoscopic port 4000, connected thereto and/or used to pressurize a body chamber via an opening or a passage in Laparoscopic port 4000 (not shown), as practiced in known laparoscopic ports designs. Valve 4200 includes an expandable, optionally inflatable, annular sealing member 4210 made of a resilient membrane and comprising an hourglass-like shaped cross section. Annular sealing member 4210 is fixated at a proximal portion thereof to portion 4260 of body 4100 inner periphery, and at a distal portion thereof to portion 4250 on projection 4140 inwardly over openings 4150, thereby creating a closed chamber opened only at its distal side with openings 4150. In some embodiments, annular sealing member 4210 is designed to inwardly expand towards its center when inflated by pressurized gas also pressurizing the body chamber, via openings 4150. A proximal shielding trigger 4220 and a distal shielding trigger 4230 are embedded in or covering, respectively, distal and proximal portions of annular sealing device 4210, leaving an uncovered central portion 4240. Uncovered portion 4240 is then applied to function as a sealing portion, similarly to either a zero type seal and/or an instrument type seal. Proximal shielding trigger 4220 and distal shielding trigger 4230 are provided unitary or as distinct objects, and are generally shaped, each, as truncated cones or domes, optionally each is provided as a single piece, or optionally slitted or optionally includes interlinked shielding members. In aspects of some embodiments of the present invention, valve 4200 incorporates at least two of sealing function, triggering and/or sensing function, centering function and seal actuating function.

In some embodiments of the invention, valve 4200 of laparoscopic port 4000 includes centering means with at least one triggering portion incorporating a trigger (e.g., distal shielding trigger 4230), and a sealing portion incorporating a seal (e.g., central portion 4240). In some embodiments of the invention, valve 4300 includes an hourglass-like shaped membrane, optionally pliable and/or elastic, comprising a distal divergent surface that is adapted to accommodate a proximally incoming artifact, a proximal convergent surface that is adapted to accommodate a distally withdrawing artifact, and a normally sealed passage provided therebetween. In some embodiments of the invention, the membrane is circumferentially connected at distal and proximal edges thereof to inner surface of the tubular member along a length of the lumen. Optionally, the membrane distal edge is connected to an inward circumferential projection of the tubular member. In some embodiments, the distal divergent surface and/or the inward circumferential projection includes at least one pore allowing inward expansion of the membrane by inflowing pressurized gas. As shown in FIG. 5A, a needle 4300 comprising a sharp tip 4310 is angularly (i.e., non-aligned with longitudinal axis of elongated body 4100) introduced in lumen 4130 from distal end 4120 towards valve 4200. The angular introduction causes needle 4300, which is substantially smaller in diameter than lumen 4130, to engage valve 4200 away from its center, namely, central portion 4240, so that it is inevitably contact distal shielding trigger 4230. Being relatively rigid or hard, distal shielding trigger 4230 prevents sharp tip 4310 from causing damage (e.g., cut or penetrate through) to the resilient membrane. Thus the shielding trigger is protecting the resilient membrane making annular sealing member 4210. Optionally, alternatively or additionally, distal shielding trigger 4230 is smooth and/or resists further angular motion of needle 4300 thereby forcing it to align and center while sliding towards central portion 4240. In some embodiments, needle 4300 presses against distal shielding trigger 4230 causing the latter to pivot outwardly and mildly compress annular sealing member 4210. In some embodiments, when being compressed, gas is forced to expel from within annular sealing member 4210 via openings 4150. In some embodiments of the invention, when annular sealing member 4210 is compressed, its central portion 4240 is forced to open hence accommodating entrance of needle 4300 therethrough. In some embodiments, when distal shielding trigger 4230 pivots outwardly and/or when annular sealing member 4210 compresses, proximal shielding trigger 4220 is also forced to pivot outwardly, and optionally vice versa.

FIG. 5B shows needle 4300 when passing through annular sealing member 4210. As shown, annular sealing member 4210 is mildly compressed and both proximal shielding trigger 4220 and distal shielding trigger 4230 are slightly outwardly pivoted, hence allowing accommodation of needle 4300 passing therethrough. Central portion 4240 inwardly and circumferentially presses against needle 4300 in a way that seals against gas leak. In FIG. 5C, needle 4300 is further advanced towards distal end 4110 while optionally maintaining at least one of an alignment with elongated body 4100 axis and air-tight sealing with central portion 4240.

In some embodiments of the invention, needle 4300 is a surgical manipulator configured for carrying and operating an end-effector, such as surgical head 4400, attachable at its tip 4310. In some embodiments, needle 4300 penetrates into the body chamber at a point distant to positioning of distal end 4120 in body chamber, and is then passable via laparoscopic port 4000 to outside environment to be connected with surgical head 4400 and then pulled back into body chamber to perform a surgical intervention. In FIG. 5D, needle 4300 is shown carrying surgical head 4400 attached over tip 4310. Since surgical head 4400 has outer diameter that is substantially greater than diameter of needle 4300, annular sealing member 4210 is further compressed to allow surgical head 4400 passage therethrough. In some embodiments, such further compression is attained by further pressing proximal shielding trigger 4220 to outwardly pivot. In some embodiments, central portion 4240 maintains air-tight sealing around circumference of surgical head 4400. Once surgical head 4400 is fully introduced and passed through sealing member 4210, the latter regains its nominal shape and expanded form as shown in FIG. 5A.

Figure 6B:
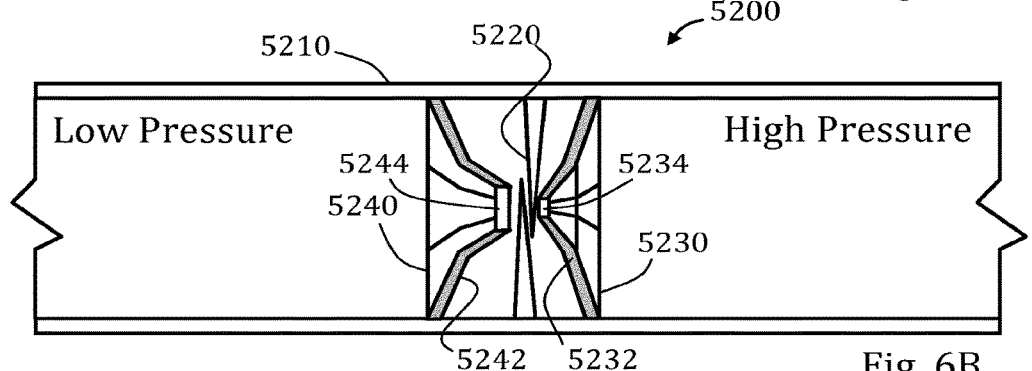

Reference is now made to FIGS. 6A-B which schematically illustrate cut views of portions of exemplary laparoscopic ports comprising distal seal protectors, in accordance with embodiments of the present invention. In FIG. 6A a portion 5110 of laparoscopic port 5100 is shown having an elongated tubular form with a lumen extending from its proximal side to its distal side. A seal 5120 is located in portion 5110 dividing it do a proximal region and a distal region and sealing the distal region such that fluids cannot escape through seal 5120 to the proximal region. Optionally and additionally, seal 5120 is configured to seal the proximal region of portion 5110 such that fluids cannot escape therethrough to the distal region of portion 5110. In some embodiments and as shown in FIG. 6A, port 5100 is provided in-between separated environments differentiated by pressures, wherein the distal region of portion 5110 is held at a higher pressure environment, such as an abdominal cavity insufflated with pressurized $CO_2$, and the proximal region of portion 5110 is under lower pressure environment, such as an outer-body environment, while seal 5120 keeps the higher pressure region sealed. A shielding trigger in the form of a seal protector 5130 is provided in portion 5110 adjacent and distal to seal 5120 in order to protect it from an incoming artifact having a free end (not shown) emerging from the high pressure environment and traveling from the distal region to the proximal region of portion 5110 through seal 5120. As previously described, an artifact according to the present invention may be a shaft of a tool manipulator passing through port 5100 from within an abdominal cavity to the outside environment, for example in order to connect an end-effector (e.g., a surgical tool such as a grasper) at its free end and possibly withdraw the assembled instrumentation back into the abdominal cavity to perform a surgical procedure. Unlike seal protectors used in some known laparoscopic ports and trocars which are intended to protect the seal from artifacts emerging and passing therethrough from the (proximal) lower pressure environment to the (distal) higher pressure environment, distal seal protector 5130 is provided in reversed mode or formation in order to facilitate an opposite artifact travel. Seal protector 5130 includes a hollow truncated conic portion 5132 directed proximally with its smaller diameter towards seal 5120. Conic portion 5132 includes a plurality of flaps and/or creases allowing it to extend laterally and open in case an artifact passes proximally pressing against it. An opening 5134 is located at conic portion 5132 apex sized according to minimal diameter of an artifact allowed to extend conic portion 5132. Seal protector 5130 may be formed of a rigid, elastic or pliable material, and for example may include a plurality of spaced lateral slits around its conic portion 5132 creating a plurality of rigid flaps. Upon proximally directed extension, conic portion 5132 forces seal 5120 to open and shields it and/or bridges across it in a distal to proximal direction to prevent damaging by the incoming artifact. As such, seal protector 5130 also functions as triggering actuator as it triggers opening of the seal hence may be considered a shielding trigger. Seal protector 5130 may be configured to also center an incoming artifact if traveling proximally therethrough.

FIG. 6B shows a second example in which two seal protectors are used, a proximal seal protector for protecting the seal from artifacts traveling distally with their free end therethrough and a distal seal protector for protecting the seal from artifacts traveling proximally, or pulled back distally into the body, with their free end therethrough. In FIG. 6B a portion 5210 of laparoscopic port 5200 is shown having an elongated tubular form with a lumen extending from its proximal side to its distal side. A seal 5220 is located in portion 5210 dividing it do a proximal region and a distal region and sealing the distal region such that fluids cannot escape through seal 5220 to the proximal region. Optionally and additionally, seal 5220 is configured to seal the proximal region of portion 5210 such that fluids cannot escape therethrough to the distal region of portion 5210. In some embodiments and as shown in FIG. 6B, port 5200 is provided in-between separated environments differentiated by pressures, wherein the distal region of portion 5210 is held at a higher pressure environment, such as an abdominal cavity insufflated with pressurized CO2, and the proximal region of portion 5210 is under lower pressure environment, such as an outer-body environment, while seal 5220 keeps the higher pressure region sealed. A distal shielding trigger in the form of a seal protector 5230 is provided in portion 5210 adjacent and distal to seal 5220 in order to protect it from incoming artifacts (not shown) emerging with a free end thereof from the high pressure environment and traveling from the distal region to the proximal region of portion 5210 through seal 5220. Seal protector 5230 includes a hollow truncated conic portion 5232 directed proximally with its smaller diameter towards seal 5220. A second proximal shielding trigger in the form of a seal protector 5240 is provided in portion 5210 adjacent and proximal to seal 5220 in order to protect it from incoming artifacts (not shown) emerging with a free end thereof from the low pressure environment and traveling from the proximal region to the distal region of portion 5210 through seal 5220. Seal protector 5240 includes a hollow truncated conic portion 5242 directed distally with its smaller diameter towards seal 5220. Any of conic portions 5232 and 5242 includes a plurality of flaps and/or creases allowing it to extend laterally and open in case an artifact passes and pressing against it. An opening 5234 is located at conic portion 5232 apex sized according to minimal diameter of an artifact allowed to extend conic portion 5232. Likewise, an opening 5244 is located at conic portion 5242 apex sized according to minimal diameter of an artifact allowed to extend conic portion 5242. Optionally and as shown, opening 5244 is larger than opening 5234 as it allows larger diameter artifacts (such as an obturator or a laparoscope) passing therethrough triggering opening of seal 5220, while opening 5234 is configured for smaller diameter artifacts (optionally less than opening 5244 diameter) to travel therethrough and trigger opening of seal 5220. Seal protector 5230 and/or seal protector 5240 may be formed of a rigid, elastic or pliable material, and for example may include a plurality of spaced lateral slits around its conic portion 5232/5242 creating a plurality of rigid flaps.

Figure 7A:
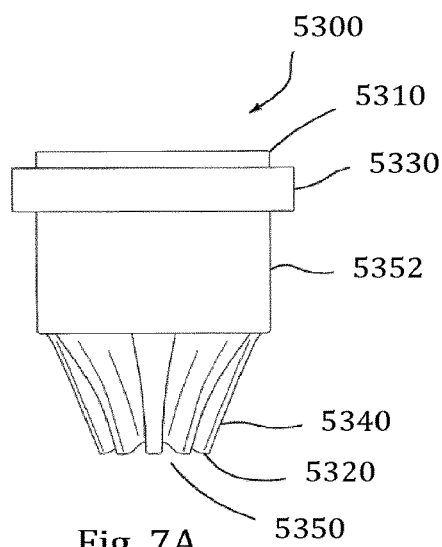
FIGS. 7A-B schematically illustrate a first and a second exemplary seal protectors, in accordance with embodiments of the present invention.
Figure 7B:
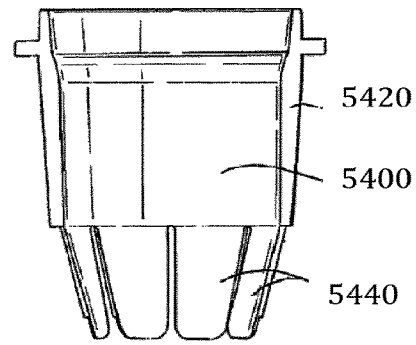

FIGS. 7A-B schematically illustrate a first and a second exemplary shielding triggers in the form of seal protectors, in accordance with embodiments of the present invention. FIG. 7A illustrates a pleated seal protector 5300 which is generally tubular with a distal end 5310 and a proximal end 5320. Distal end 5310 comprises an optional radial flange 5330 to engage a corresponding recess and secure in-place, optionally to laparoscopic port wall. Proximal end 5320 is frustoconical, tapered, and/or funnel-shaped, and comprising a plurality of convergent longitudinal pleats 5340, terminating in an opening 5350. A generally cylindrical entry region 5352 extends between distal end 5310 and proximal end 5320. In other embodiments, the entry region 5352 has another suitable shape, for example, frustoconical, an elliptical cross section, a polygonal prism, and/or pyramidal. Some embodiments do not comprise an entry region 5352. Seal protector 5300 may be formed of any suitable resilient material, for example, a polymer. Suitable polymers include polyolefins, polyethylene, polypropylene, polyvinyl chloride (PVC), polytetrafluoroethylene (PTFE), polyimide (Nylon®, Delrin®), copolymers, blends, mixtures, and the like. In some embodiments, seal protector 5300 includes a spring metal, and/or a composite; optionally it is monolithic and/or integrally manufactured; optionally comprising a non-elastomeric material, optionally at least in a portion thereof which defines opening 5350 for reducing instrument drag compared with elastomeric materials, particularly on passing instruments therethrough. Seal protector 5300 is configured to protect a distal end of laparoscopic seal (such as a zero seal, a septum seal, a wiper seal and/or an instrument seal, optionally a single seal or a series of seals). The seal is then protected from damage when an instrument is inserted through the distal end of a laparoscopic port or trocar, as it comprises relatively soft materials so an instrument tip forced against it can tear and/or damage the material. Seal protector 5300 is configured to direct such an instrument towards the center or the opening of a seal if it is angled with respect to port axis and the frustoconical shape of the proximal end 5320 directs the instrument tip towards the opening 5350 as the instrument is advanced. The pleats 5340 (shown in their relaxed state) permit the opening 5350 at the proximal end to expand and contract around an instrument as the instrument is advanced therethrough.

FIG. 7B illustrates a rigid seal protector 5400 to protect a seal, such as a septum seal, during the insertion and removal of surgical instruments. Seal protector 5400 includes a tubular member 5420 having a proximal end and a distal end, and a plurality of blades or leaflets 5440 protruding from the proximal end of the tubular member 5420. Seal protector 5400 may be formed of a rigid plastic cylinder, which operates to center and guide an instrument as it is inserted with a free end thereof from the distal end of the laparoscopic port and engages the laparoscopic seal. Optionally and alternatively (not shown), the blades or leaflets 5440 may overlap one another. In order to avoid potential "lock-up" as instruments are withdrawn back into the abdominal cavity, seal protector 5400 is optionally designed to deform at the tip of each blade or leaflet 5440 such that each individual leaflet's tip will roll inward toward the instrument and create a variable radius for the instrument to glide on as it is removed from the seal. As the tip of each leaflet is deformed inward, the bodies of the blades or leaflets 5440 are forced away from the axial position of the instrument.

Figure 8A:
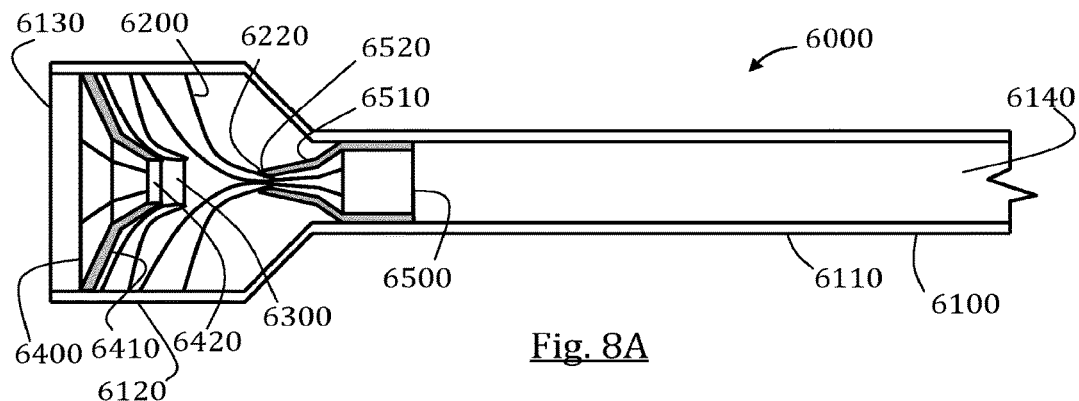
FIGS. 8A-C schematically illustrate an exemplary laparoscopic port comprising a sealing assembly with two-side protection, in accordance with embodiments of the present invention.
Figure 8B:
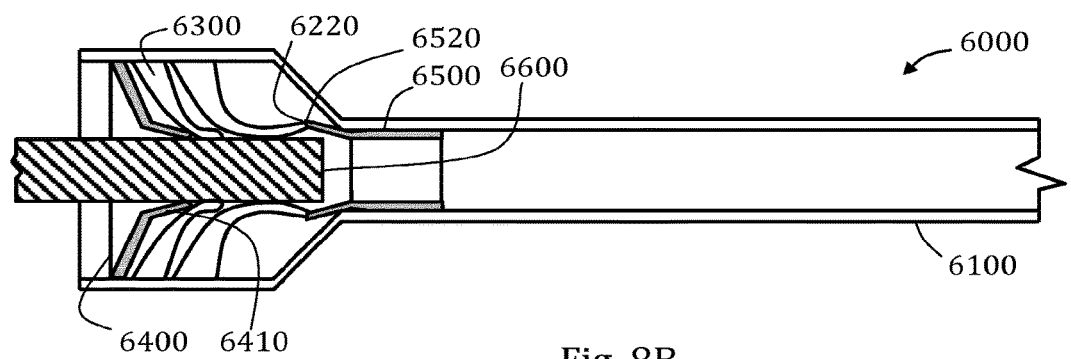
Figure 8C:
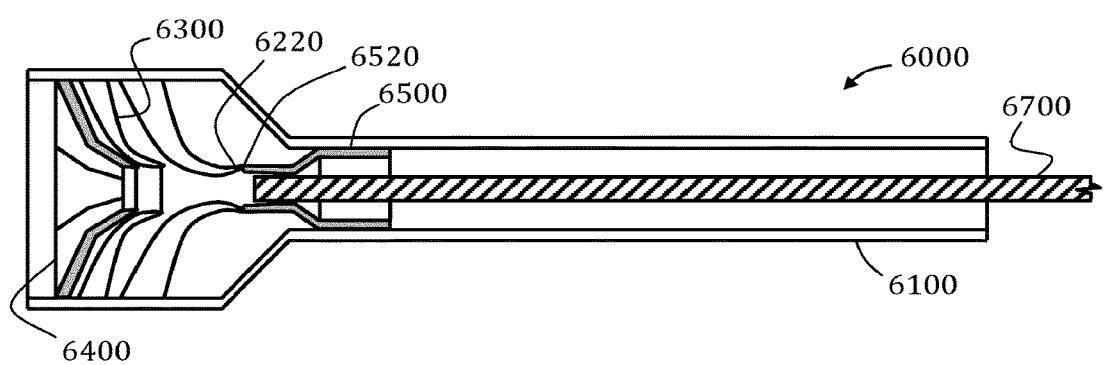

FIGS. 8A-C schematically illustrate an exemplary laparoscopic port 6000 comprising a valve with two-side protection, in accordance with embodiments of the present invention. Laparoscopic port 6000 is formed as a trocar comprising an elongated tubular member 6100 having a large diameter proximal region 6120 and a small diameter distal region 6110 and defining a lumen 6140 passing therethrough from a proximal opening 6130 to a distal opening (not shown). Laparoscopic port is configured for placement via a surgical opening in a patient's abdomen, such that its distal end protrudes in the abdominal cavity. Laparoscopic port 6000 houses at its proximal region 6120 a valve comprising a plurality of seals distributed sequentially including a proximal septum or instrument seal 6300 and a distal duckbill or zero seal 6200. A proximal shielding trigger in the form of a proximal seal protector 6400 is positioned adjacent and proximally to instrument seal 6300 and optionally sized and shaped for optionally converging and/or at least partially nesting in instrument seal 6300. Proximal seal protector 6400 optionally includes a plurality of rigid leaflets 6410 projecting distally and normally closed to a frustoconical configuration with a distal opening 6420. A distal shielding trigger in the form of a distal seal protector 6500 is provided adjacent and distally to zero seal 6200, reversely oriented to proximal seal protector 6400 and optionally also to zero seal 6200 and/or instrument seal 6300. Distal seal protector 6500 optionally includes a plurality of rigid leaflets 6510 projecting proximally and normally closed to a frustoconical configuration. In some embodiments, the tips 6520 of leaflets 6510 are connected to corresponding lip end of zero seal 6200, such that opening/closing of one member causes opening/closing of the other member. FIG. 8B shows a first scenario where an artifact 6600 such as an obturator is passed in lumen 6140 from proximal opening 6130 and distally thereby laterally extending leaflets 6410 and stretching out instrument seal 6300 to cause peripheral sealing. Further pushing artifact 6600 distally will cause zero seal 6200 to open while also laterally extending leaflets 6510 as needed. In this scenario the proximal seal protector 6400 served to protect instruments seal 6300 while distal seal protector 6500 was ineffective yet did not interfere with artifact progression or sealing properties. FIG. 8C shows a second scenario where an artifact 6700 such as a slender shaft travels proximally in lumen 6140 from the distal opening of port 6000 thereby laterally extending leaflets 6510 and opening (e.g., stretching out) zero seal 6200. In some embodiments, instrument seal 6300 and proximal seal protector 6400 has minimal opening at their relaxed contracted state which is similar or larger than artifact 6700 maximal diameter so further passing it therethrough will not cause any effect. Optionally and alternatively, instrument seal 6300 and proximal seal protector 6400 has minimal opening at their relaxed contracted state which is smaller than artifact 6700 maximal diameter yet they are configured to allow passing therethrough with no damage, at least in case that artifact 6700 is centered and aligned to port 6000 longitudinal axis, optionally by the distal seal protector 6500 and/or by other centering means. In this scenario the distal seal protector 6500 served to protect zero seal 6200 while proximal seal protector 6400 was ineffective yet did not interfere with artifact progression or sealing properties.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A laparoscopic port, comprising:
   a tubular member comprising a proximal end and a distal end and a lumen extending therebetween;
   at least one seal member provided in said lumen, the at least one seal member including a duckbill or zero seal to prevent pressurized gas flow from said distal end to said proximal end of said tubular member; and
   a shielding trigger positioned distal to said seal member in said lumen, said shielding trigger being shaped so as at least a proximal portion of said shielding trigger has a narrowing cross-section that extends towards said seal member, said proximal portion is adapted to actuate a reversible opening and protection of said seal member upon a proximally projected pressure from a distal end of an artifact,
   wherein the seal member comprises a distal divergent surface adapted to accommodate a proximally incoming artifact, a proximal convergent surface adapted to accommodate a distally withdrawing artifact, and a normally sealed passage provided therebetween.

2. The laparoscopic port according claim 1, wherein the shielding trigger is made of a hardened material and/or a reinforced pliant or semi-pliant material.

3. The laparoscopic port according to claim 1, further comprising a centering means adapted to align said artifact in a chosen alignment.

4. The laparoscopic port according to claim 3, wherein the chosen alignment is concentric with an axis of the lumen.

5. The laparoscopic port according to claim 3, wherein said centering means are provided on said artifact.

6. The laparoscopic port according to claim 3, wherein the centering means are provided in the lumen and distal to the shielding trigger.

7. The laparoscopic port according to claim 3, wherein the centering means comprise an expandable portion.

8. The laparoscopic port according to claim 7, wherein the expandable portion is inflatable.

9. The laparoscopic port according to claim 3, wherein the shielding trigger is the centering means.

10. The laparoscopic port according to claim 1, wherein the shielding trigger is embedded in or covering the distal divergent surface of said seal member.

11. The laparoscopic port according to claim 1, wherein the shielding trigger is pliable and/or pivotable outwardly thereby actuating the reversible opening by compressing the seal member.

12. The laparoscopic port according to claim 1, wherein the port comprises a second shielding trigger embedded in or covering a proximal divergent surface of the seal member to actuate a reversible opening and protection of the seal member when withdrawing the artifact.

13. The laparoscopic port according to claim 1, wherein at least said proximal portion of the shielding trigger is shaped as a truncated cone or dome or frustoconical or funnel shaped or tapered when closed.

14. The laparoscopic port according to claim 13, wherein the shielding trigger is a single piece, or slitted or interlinked shielding members.

15. The laparoscopic port according to claim 1, wherein the shielding trigger comprises a tubular portion.

16. The laparoscopic port according to claim 15, wherein the shielding trigger comprises a plurality of flaps or creases or pleats or blades or leaflets protruding from a proximal end of the tubular portion to allow said shielding trigger to laterally extend and thereby actuating the reversible opening and protection of the seal member upon proximally projected pressure from the distal end of the artifact.

17. The laparoscopic port according to claim 15, wherein the shielding trigger is made of a rigid material and/or elastic material and/or pliable material and/or a spring metal and/or a composite material.

18. The laparoscopic port according to claim 15, wherein the port comprises a second shielding trigger positioned proximal to the seal member to actuate a reversible opening and protection of said seal member or of a second seal member proximal to said seal member, when withdrawing the artifact.

19. The laparoscopic port according to claim 1, wherein the shielding trigger is positioned distally to the duckbill or zero seal.

* * * * *